(12) United States Patent
Koyama et al.

(10) Patent No.: US 7,104,954 B2
(45) Date of Patent: Sep. 12, 2006

(54) LIVING BODY MEASUREMENT APPARATUS

(75) Inventors: Kazuyasu Koyama, Tokyo (JP); Fumiko Nakagawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 266 days.

(21) Appl. No.: 10/458,377

(22) Filed: Jun. 11, 2003

(65) Prior Publication Data

US 2003/0229275 A1    Dec. 11, 2003

(30) Foreign Application Priority Data

Jun. 11, 2002   (JP)   ............................. 2002-169512

(51) Int. Cl.
*A61B 5/00* (2006.01)

(52) U.S. Cl. ...................... 600/300; 600/547

(58) Field of Classification Search ........ 600/300–301, 600/547, 551, 591, 587; 128/920–925, 897–898; 340/573.1; 177/245, 25.11–25.19, 26, 264

See application file for complete search history.

(56) References Cited

U.S. PATENT DOCUMENTS 6,480,736 B1   11/2002   Kodama et al.
6,656,130 B1 *  12/2003   Takehara et al. ............. 600/551

FOREIGN PATENT DOCUMENTS

| EP | 1 075 858 | 2/2001 |
|---|---|---|
| EP | 1 132 046 | 9/2001 |
| EP | 1 192 903 | 4/2002 |
| JP | 5-49050 | 7/1993 |
| JP | 07 171120 | 7/1995 |
| JP | 2002-112982 A | 4/2002 |

\* cited by examiner

*Primary Examiner*—Max F. Hindenburg
*Assistant Examiner*—Michael Astorino
(74) *Attorney, Agent, or Firm*—McDermott Will & Emery LLP

(57) ABSTRACT

Disclosed is a living body measurement apparatus, comprising: an input unit; a measurement unit; an arithmetic unit; and a display unit. According to the present invention said input unit enters body information for a person under test, and said measurement unit measures physical characteristic for the person under test. Furthermore, said arithmetic unit calculates an index of body composition for the person under test based on the entered body information and the measured physical characteristic, and said display unit displays the calculated index of body composition by using an animation in such manner that the animations is differently displayed according to the result of calculation by said arithmetic unit.

6 Claims, 24 Drawing Sheets

ALTERNATELY DISPLAYED

LIVING BODY MEASUREMENT APPARATUS

BACKGROUND OF THE INVENTION

1. Field of the Invention

The present invention relates to a display format for a living body measurement apparatus for measuring physical characteristic for a person under test and for calculating body composition based on the measured value.

2. Prior Art

Various types of apparatus have been known in the art for calculating an index of living body composition such as body fat rate, visceral fat level, basal metabolism, etc., using bioelectrical impedance. Such apparatus are considered useful for health care and become popular in home use.

Previous measurement apparatus have generally been designed to display the measurement result in numerical value. Accordingly, a person under test, if having no expert skill, could not immediately decide whether the value is higher or lower. Therefore, it was common that the decision of whether the result is normal or not is made with reference to a table or a brochure listing some standard values, for example.

Another type of apparatus has been proposed that is configured to display a graph showing the progress of body condition up to now, together with the past data.

However, such apparatus was defective in that even if the person can see the measurement result it is very difficult to determine whether the body condition for the person is normal or not based on the measurement result.

In case of further apparatus that has been proposed to display a plurality of living body compositions, because of several numerical values simply displayed for those body compositions, it was difficult for a person under test to immediately understand which of the values is higher than normal. In addition, it was hard for the person to memorize all the values and to remain them in his memory. Accordingly, irrespective of a plurality of living body compositions displayed with much effort, they actually have not fully been utilized for health care.

Furthermore, display of the measurement result in numerical value was especially devoid of interest and was the cause for getting tired of the measurement. Therefore, there was such tendency that the measurement apparatus such as a body fat meter and a visceral fat meter that are necessary for health care during longer period of time by continuous measurement is used only once and thereafter it is not used at all. From the viewpoint of health care it is hard to say that the previous measurement apparatus has properly been utilized.

In addition, a child who has not yet learned the numerals could not understand the measurement result displayed in numerical value. Therefore, the child had no way for understanding it, except for asking the parent, for example.

Further type of apparatus has been proposed wherein some letters are used to represent what measurement result is displayed. However, such apparatus has not fully been utilized by the foreign people who do not read the letters because they could not understand the meaning of the measurement result.

In view of the above an object of the present invention is to provide a new and improved measurement apparatus for outputting the measurement result for living body composition, which is displayed not only in numerical value, but also in visually understandable manner, and which can be understood by any person under test and can be memorized as some visual image.

Displaying the measurement result with great interest makes possible for a person under test to continue the measurement, which is consequently useful for health care for longer period of time.

SUMMARY OF THE INVENTION

In order to attain such object the present invention provides a living body measurement apparatus, comprising: an input unit; a measurement unit; an arithmetic unit; and a display unit, wherein said input unit enters body information for a person under test, said measurement unit measures physical characteristic for the person under test, said arithmetic unit calculates an index of body composition for the person under test based on the entered body information and the measured physical characteristic, and said display unit includes a display section that displays the calculated index of body composition by using an animation in such manner that the animations is differently displayed according to the result of calculation by said arithmetic unit. Therefore, any person under test can readily understand the measurement result produced by the apparatus.

According to one embodiment of the living body measurement apparatus the display unit also displays some numerical value representing the calculated index of body composition. Thus, the person under test can also understand the measurement result more concretely.

According to another embodiment of the living body measurement apparatus the index of body composition is of body fat for the person under test and the display unit simultaneously displays a plurality of characters each having different lateral width, the relevant one of which is selected according to the calculated body fat value to indicate the result of body fat for the person under test. Therefore, the person under test can readily understand the body fat condition.

According to further embodiment of the living body measurement apparatus the index of body composition is of visceral fat for the person under test and the display unit specifically displays an abdominal region of the character in enlarged view and identifies it by different color selected according to the calculated visceral fat value to indicate the result of visceral fat for the person under test. Therefore, the person under test can readily understand the visceral fat condition.

According to yet further embodiment of the living body measurement apparatus the index of body composition is of basal metabolism for the person under test and the display unit changes the number of flame marks according to the calculated basal metabolism value to indicate the result of basal metabolism for the person under test. Therefore, the person under test can readily understand the basal metabolism condition.

According to yet further embodiment of the living body measurement apparatus the index of body composition is of muscle for the person under test and the display unit changes the thickness of an upper arm of the character according to the calculated muscle value to indicate the result of muscle for the person under test. Therefore, the person under test can readily understand the muscle condition.

BRIEF DESCRIPTION OF THE DRAWINGS

Now, the present invention will be described with reference to the accompanying drawings in which.

DESCRIPTION OF THE PREFERRED EMBODIMENTS

A living body measurement apparatus according to the present invention is configured to display the measurement result for an index of body composition with the use of an animation (a moving image) so that a person under test can imagine how large the measurement result is, whereby the person under test can readily grasp the measurement result for an index of body composition.

Now, an embodiment of the present invention will be described in more detail with reference to the accompanying drawings.

Figure 1:
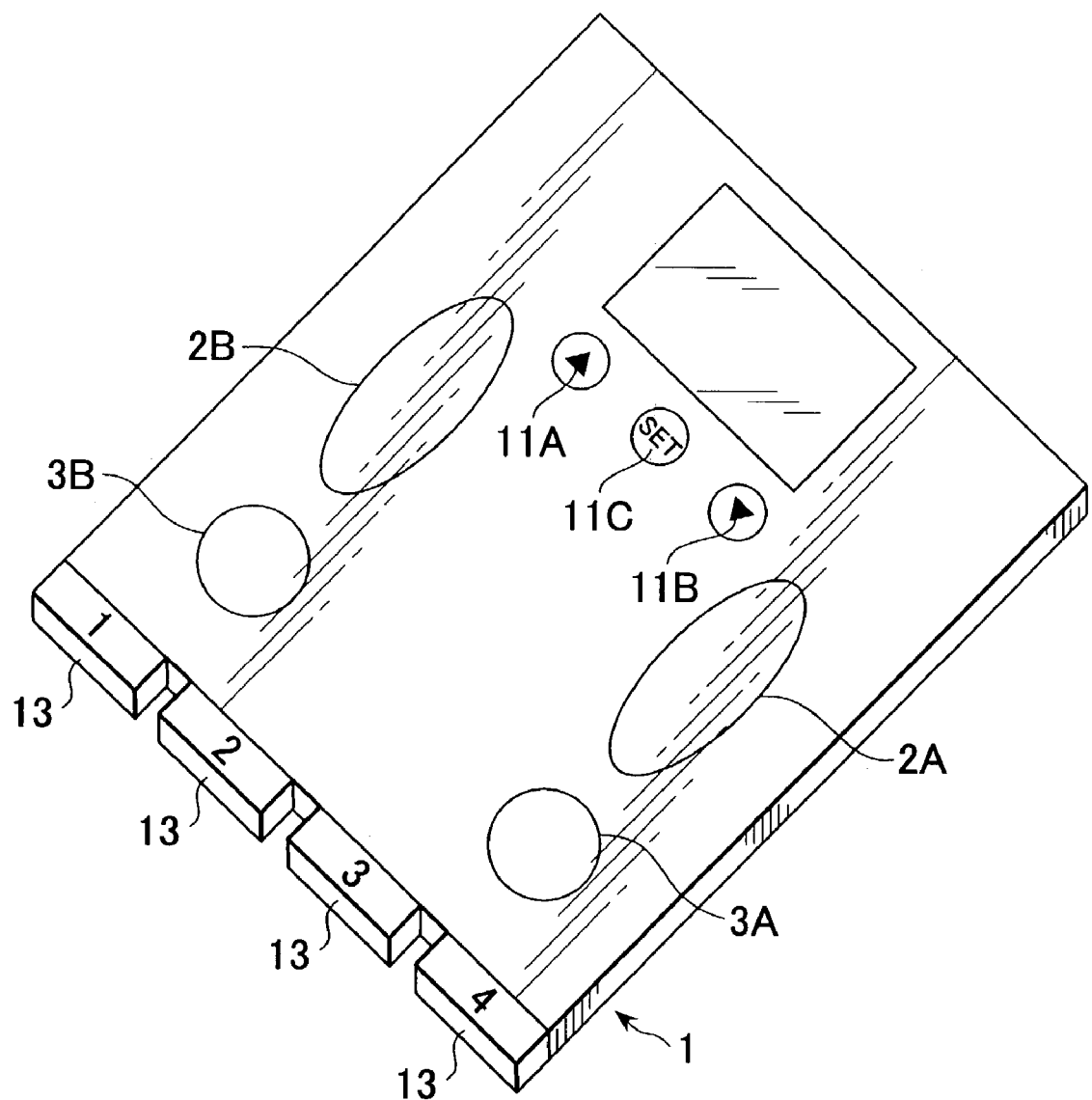
FIG. 1 is an external perspective view of a living body measurement apparatus according to one embodiment of the present invention.
Figure 2:
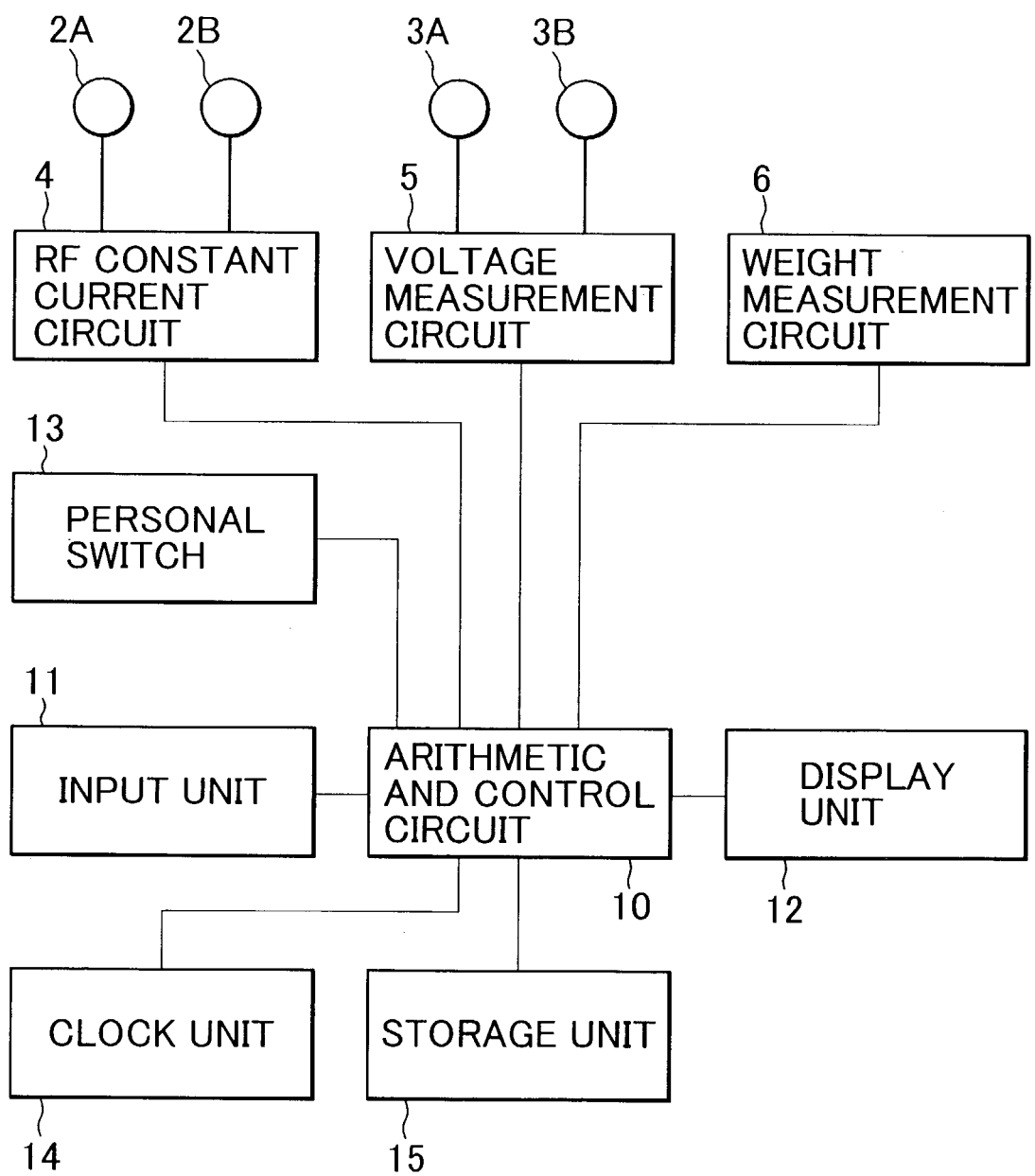
FIG. 2 is a block diagram illustrating electrical connections between main components within the living body measurement apparatus.

FIG. 1 is an external perspective view illustrating a living body measurement apparatus 1 that is capable of measuring body composition for a person under test such as body weight, body fat rate, visceral fat level, basal metabolism, amount of muscle, etc., constructed according to one embodiment of the present invention. FIG. 2 is a block diagram illustrating electrical connections between main components within the living body measurement apparatus 1 as shown in FIG. 1.

An upper surface of the living body measurement apparatus 1 is provided with four electrodes: a pair of current supplying electrodes 2A and 2B as well as a pair of voltage measurement electrodes 3A and 3B, which act as impedance measurement means for measuring the impedance between both feet of a person under test.

The pair of current supplying electrodes 2A and 2B is electrically connected with an RF constant current circuit 4 for supplying a weak RF constant current thereto. Another pair of voltage measurement electrodes 3A and 3B is electrically connected with a voltage measurement circuit 5 for measuring any voltage drop caused by said constant current. The living body measurement apparatus 1 further comprises a weight measurement circuit 6 for measuring the body weight of the person under test when he or she mounts the apparatus 1. The voltage measurement circuit 5 and the weight measurement circuit 6 are electrically connected with an arithmetic and control circuit 10 for performing various arithmetic and control operations such as analog/digital conversion, calculation of each of body compositions, etc.

The living body measurement apparatus 1 further comprises an input unit 11 including three switches: an up-switch 11A, a down-switch 11B and a setting switch 11c. Additionally, the apparatus 1 comprises a display unit 12 for displaying the entered personal body information, the measured body weight, the result of calculation, etc.

A plurality of personal switches 13 are provided on a front edge of the apparatus 1. In order to start the measurement one of the personal switches 13 is depressed to retrieve the data corresponding to that personal switch from a storage unit 15.

The living body measurement apparatus 1 further comprises a clock unit 14 for clocking the time and a storage unit 15 for storing the information such as personal data for a plurality of persons and a program for operating animations displayed on the display unit.

Figure 3:
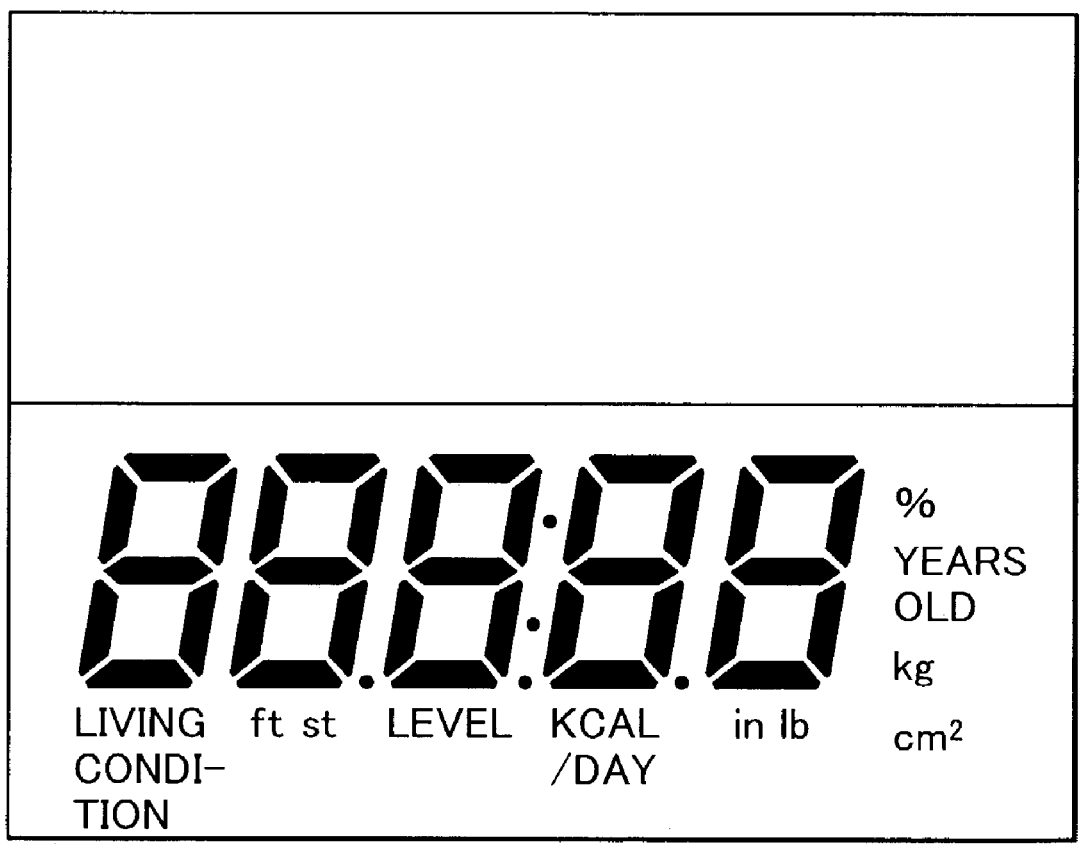
FIG. 3 is an enlarged view of a display unit of the living body measurement apparatus.

FIG. 3 is an enlarged view of the display unit 12. In particular, the display unit 12 includes an upper section or a dot-matrix display section for displaying various kinds of animations, and a lower section or a segmented display section for displaying calculated index values of living body compositions for a person under test.

Figure 4:
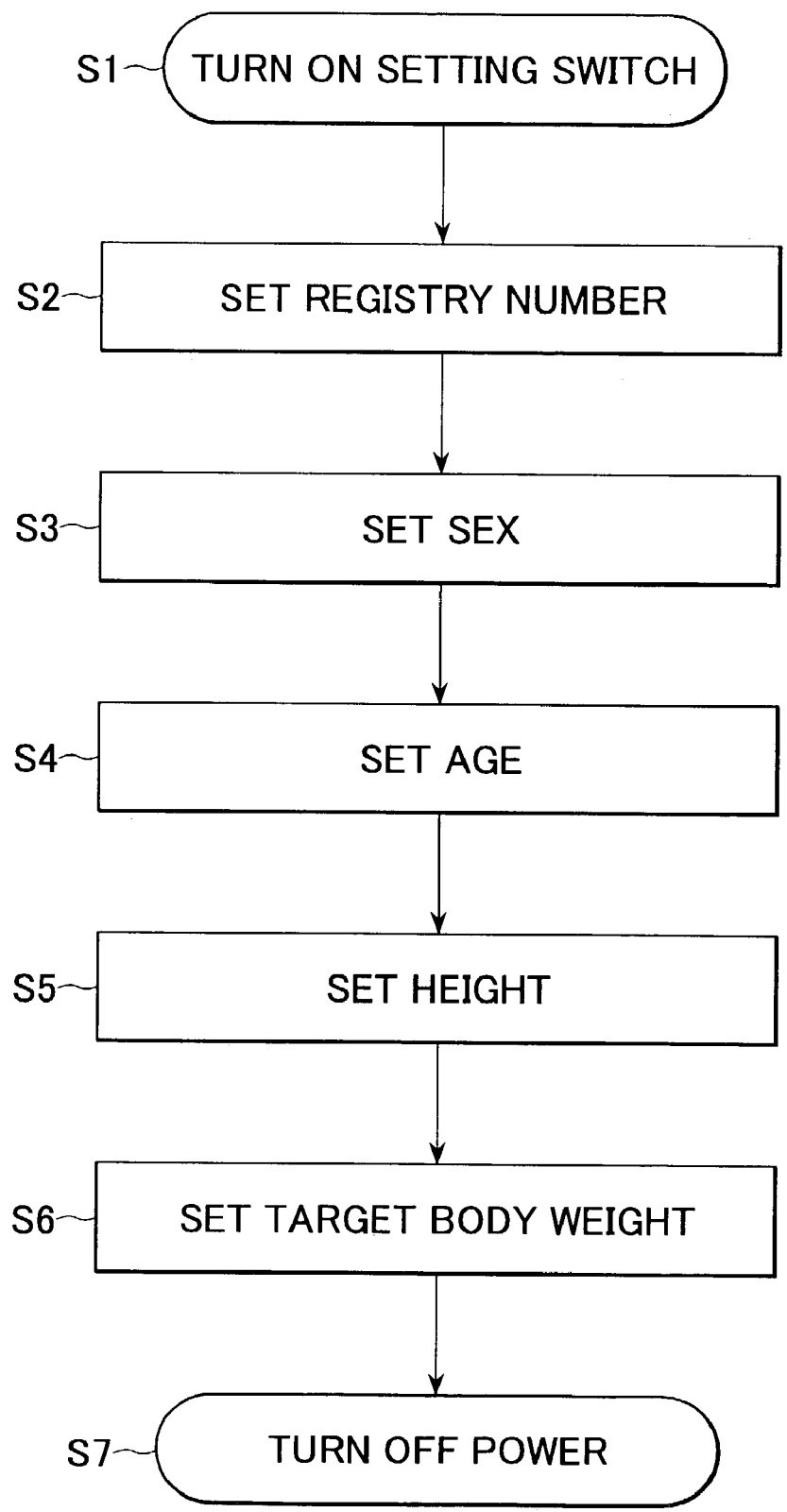
FIG. 4 is a flow chart illustrating a process for setting the personal data on the living body measurement apparatus.
Figure 5:
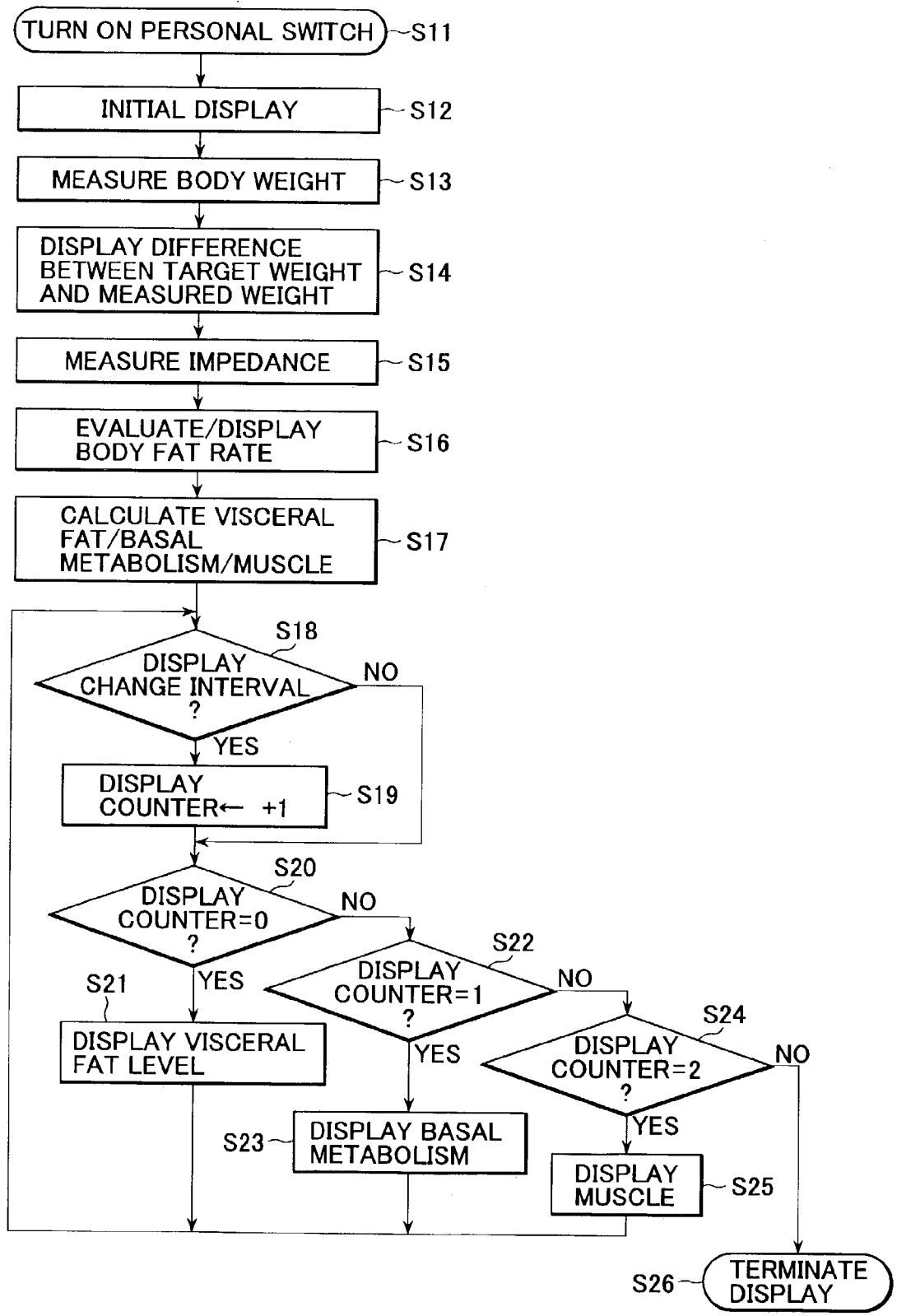
FIG. 5 is a flow chart illustrating operation steps of the living body measurement apparatus when the measurement is conducted.

Now, an operation of the living body measurement apparatus configured as described above will be described with reference to flow charts in FIGS. 4 to 5 and display screen views in FIGS. 6 to 34.

When a person under test conducts the measurement for the first time then he or she should perform setting of personal body information on the living body measurement apparatus 1 in advance.

Figure 6:
FIG. 6 is a display screen on a display unit of the living body measurement apparatus for entering a personal registration number.

When depressing the setting switch 11C the living body measurement apparatus 1 enters the setting mode. Then, some display for prompting the person under test to enter own personal registration number is presented on the display unit 12, as shown in FIG. 6 (Step S1).

Figure 7:
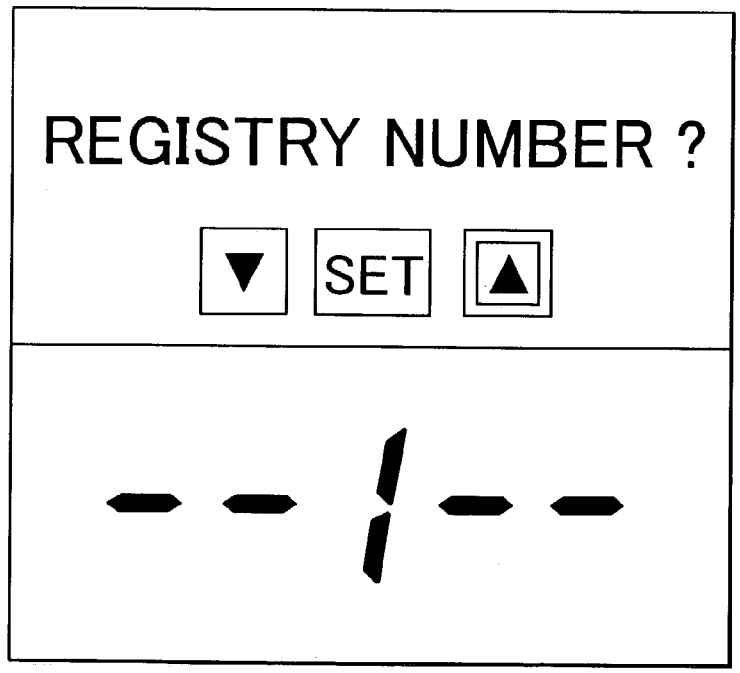
FIG. 7 is a display screen when the personal registration number is entered.
Figure 8:
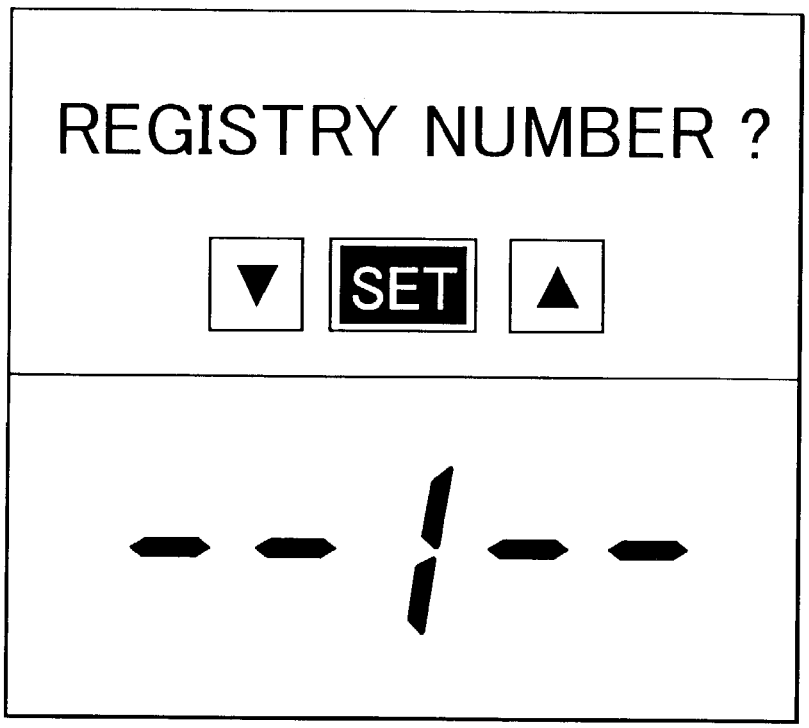
FIG. 8 is a display screen after the personal registration number has been set.

The person under test changes the number displayed in the lower stage of the display unit 12 using the up-switch 11A or the down-switch 11B. In this connection, it is noted that a portion on the display screen showing the switch that is depressed is displayed in black/white inversion, as shown in FIG. 7. When depressing the setting switch 11C once again it is displayed in black/white inversion, as shown in FIG. 8, which means that the number is set. In this example, the number "1" is selected.

Figure 9:
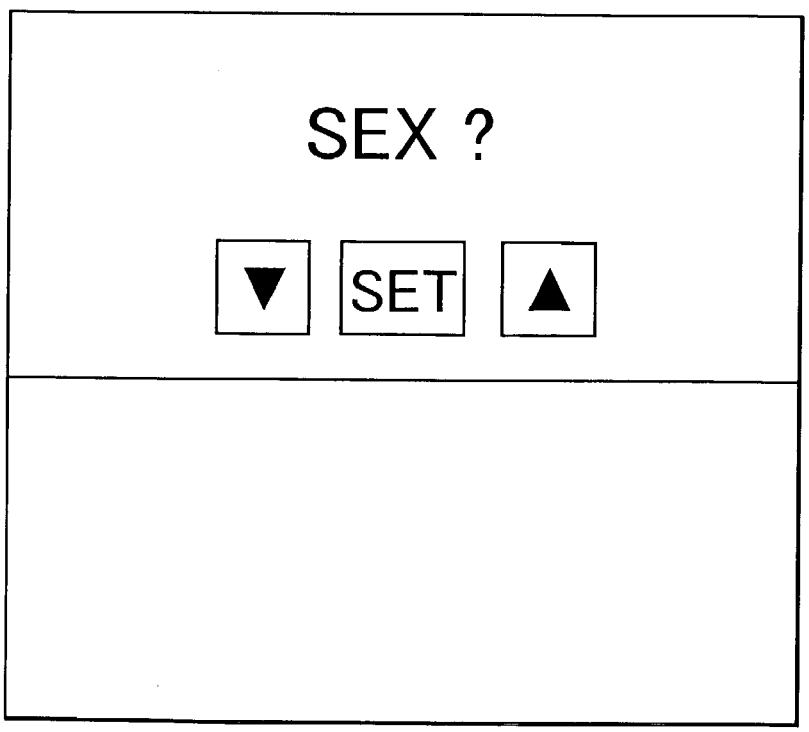
FIG. 9 is a display screen for setting the sex of the person.
Figure 10:
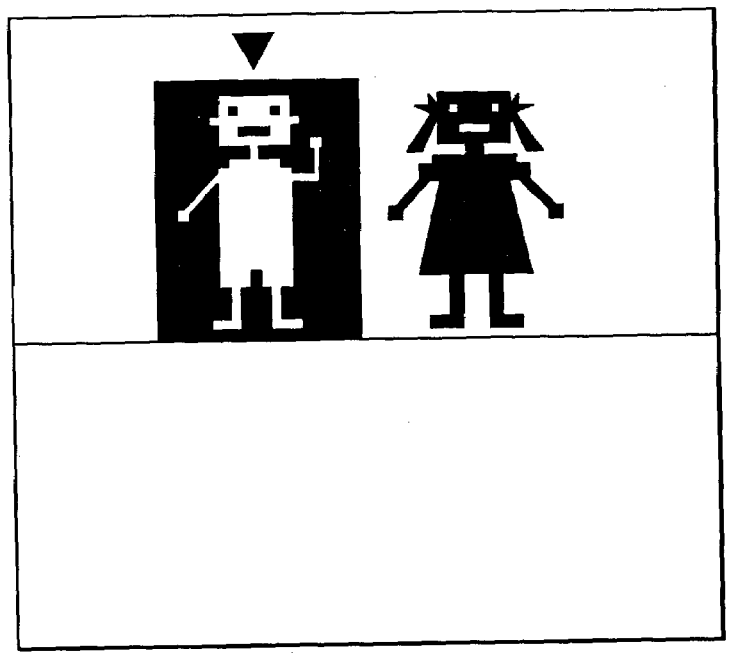
FIG. 10 is a display screen when the sex of the person is selected.

Next, the person under test performs setting of the sex. Some display for prompting the person under test to enter the sex is presented on the display screen, as shown in FIG. 9, and thereafter, characters representing "male" and "female" persons are displayed, as shown in FIG. 10. When depressing either one of the up-switch 11A and the down-switch 11B the corresponding character is selected and displayed in black/white inversion. When depressing the setting switch 11C the sex of the person under test is set.

Figure 11:
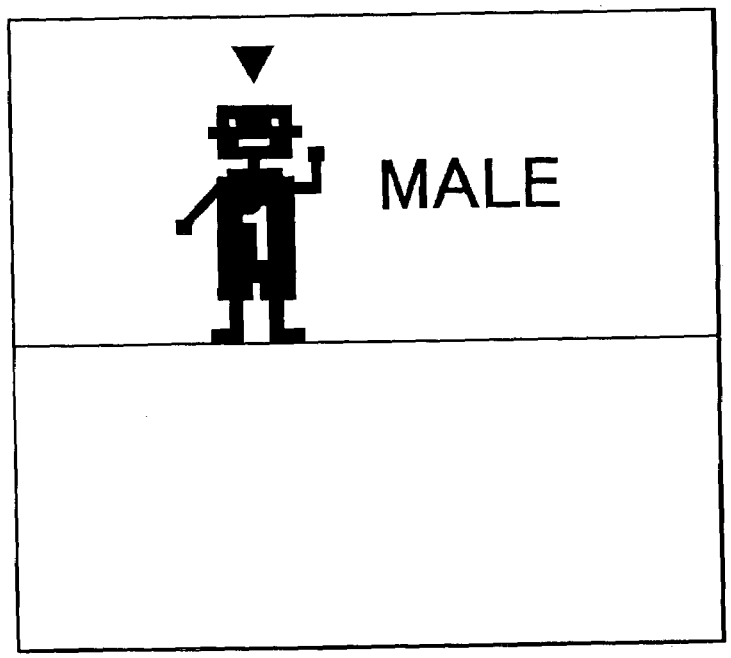
FIG. 11 is a display screen after "MALE" has been set for the sex of the person.
Figure 12:
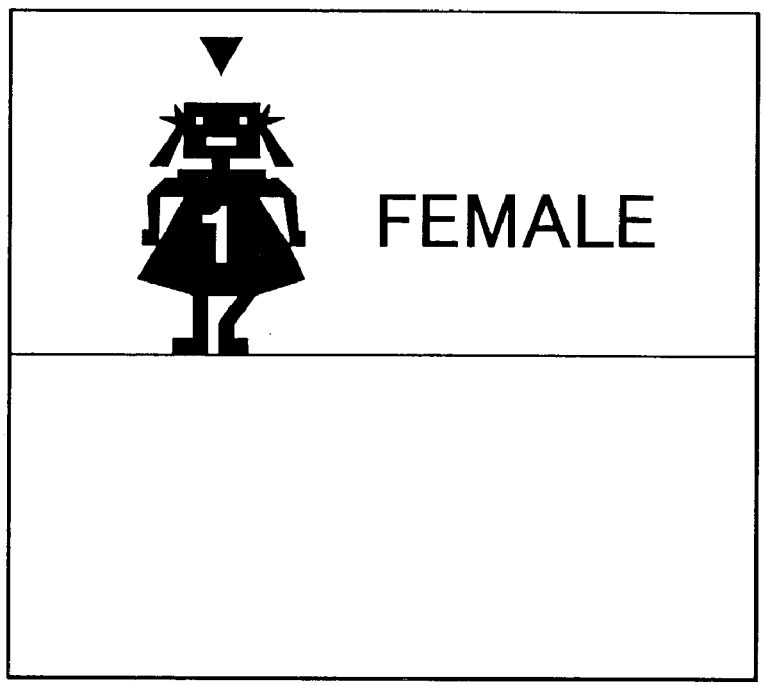
FIG. 12 is a display screen after "FEMALE" has been set for the sex of the person.

When the male is selected the letters "MALE" are also displayed, as shown in FIG. 11. The male character displayed with an arm thrown up indicates that the sex is set at "male". On the other hand, when the female is selected the letters "FEMALE" are also displayed, as shown in FIG. 12. The female character displayed with the skirt tucked up indicates that the sex is set at "female". The number shown within the contour of the character is the personal registration number. (Step S3)

Figure 13:
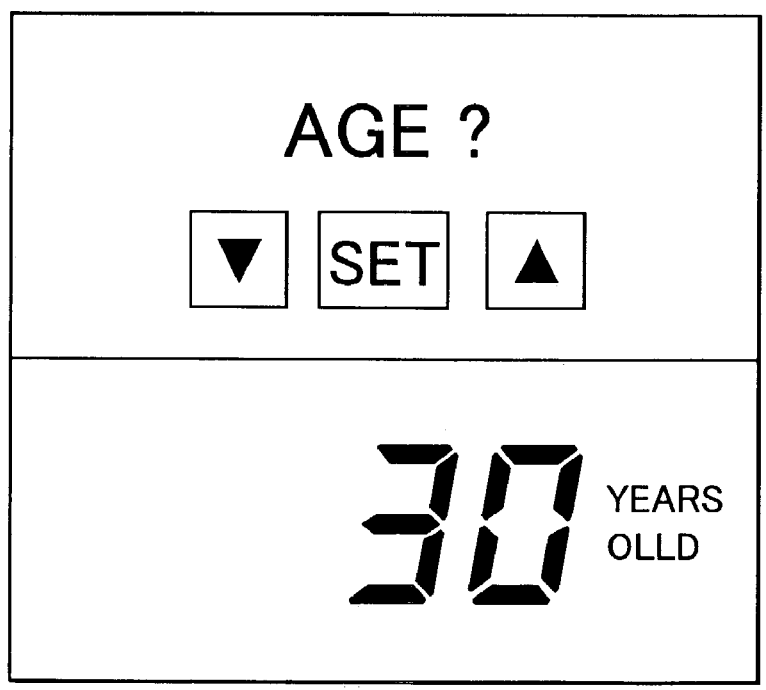
FIG. 13 is a display screen for setting the age of a person.
Figure 14:
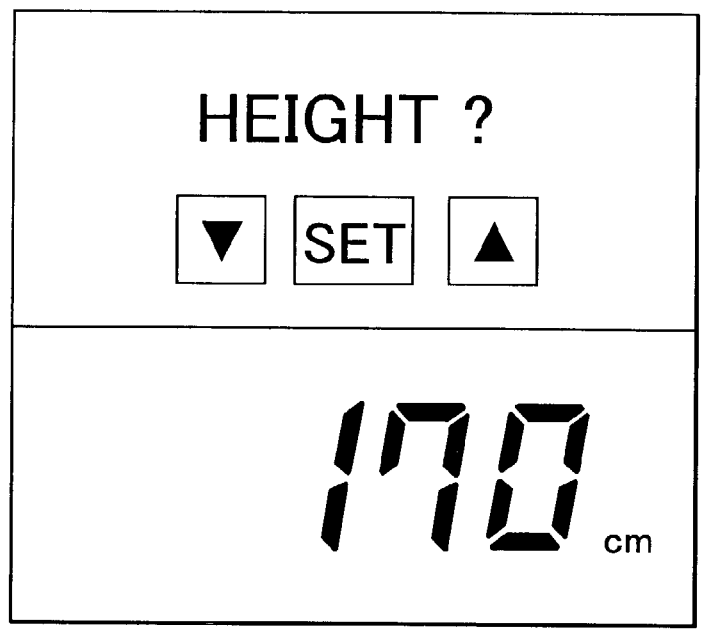
FIG. 14 is a display screen for setting the height of a person.

In the same manner, setting of other personal information such as age, height, etc. displayed on the display unit 12 is performed and such personal information is stored in the storage unit 15 (Steps S4 to S5). FIG. 13 is a display screen view when setting of the age is performed, and FIG. 14 is a view when setting of the height is performed.

Figure 15:
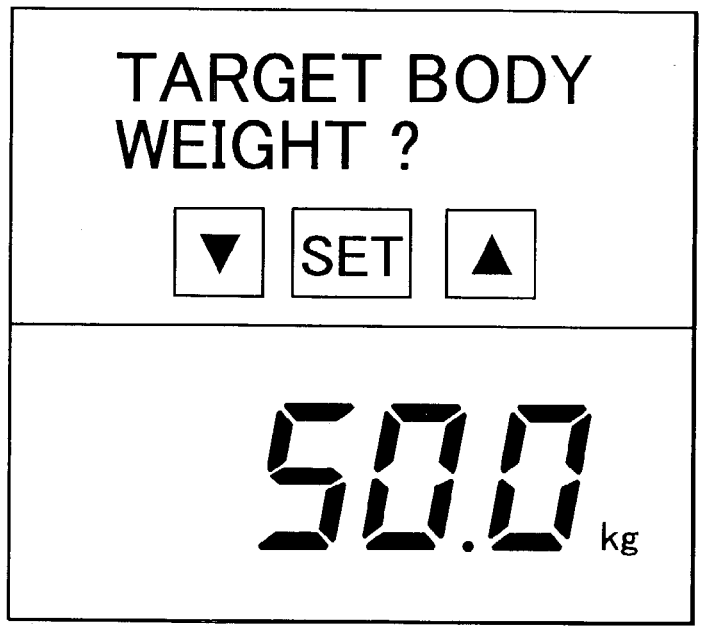
FIG. 15 is a display screen for setting the target body weight of a person.

After completion of setting of the personal body information the person under test then performs setting of the target body weight, as shown in FIG. 15. The target body weight is defined, here, as a body weight that the person under test desires to reach (Step S6).

Figure 16A:
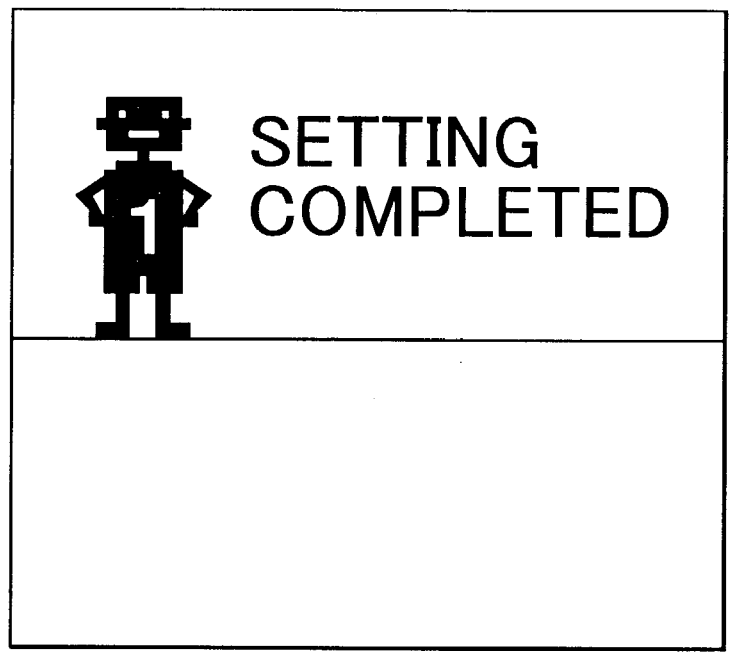
FIGS. 16A and 16B are a display screen at completion of the setting mode of the living body measurement apparatus.
Figure 16B:
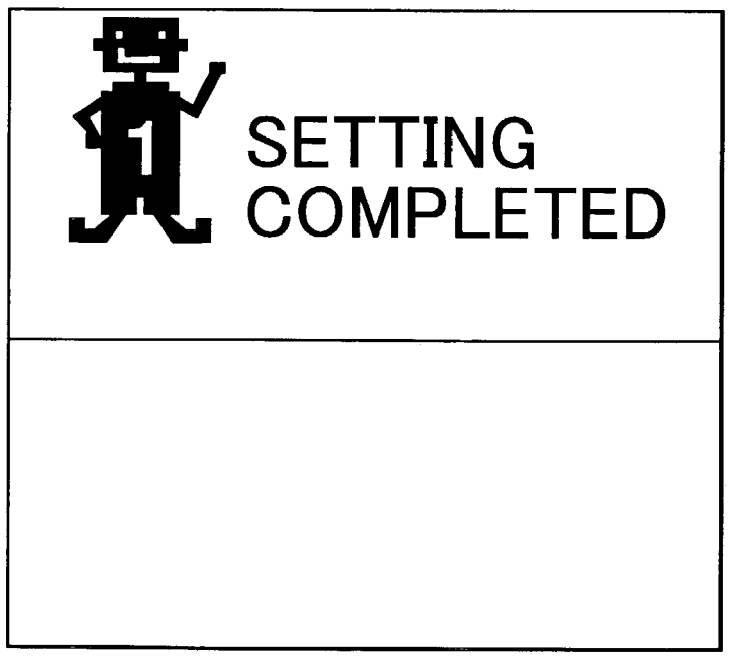

After completion of all the settings the character with sex set in Step S3 is displayed, together with the letters "SETTING COMPLETED", and the character, when jumping, indicates completion of the setting operations. FIG. 16A shows the character who is not yet jumping, and FIG. 16B shows the character who is jumping. Transition of the display from FIG. 16A to FIG. 16B is performed using gradually varying animations. Thereafter, the display disappears automatically and the setting mode is exited (Step S7).

Now, a measurement mode of operation of the living body measurement apparatus will be described in more detail.

Figure 17:
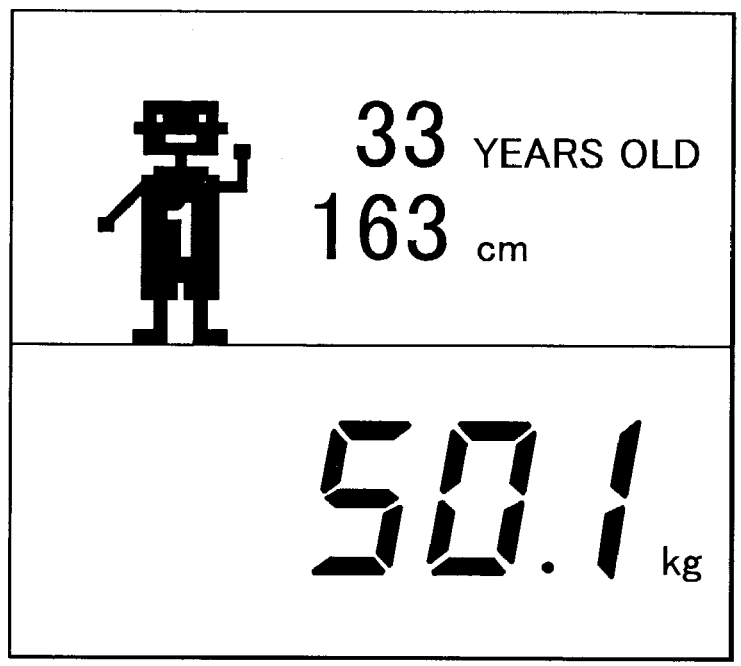
FIG. 17 is a display screen on which the content of registered information is displayed.
Figure 18:
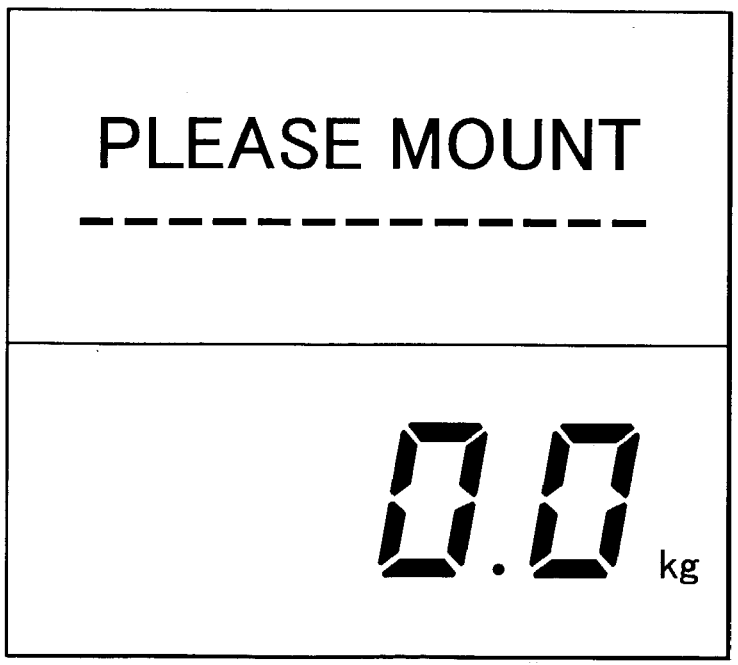
FIG. 18 is a display screen when measurement mode of the living body measurement apparatus is started.

When depressing any one of the personal switches 13 (Step S11) the personal body information corresponding to the personal registration number for that switch is retrieved from the storage unit 15 and displayed on the display unit 12. FIG. 17 is a screen display view illustrating the case wherein a person registered as the personal registration number 1 is one whose sex is male, the age is 33 and the height is 163 cm. The number displayed on the lower section of the display unit indicates the target body weight. Thereafter, an instruction for directing the person under test to mount the living body measurement apparatus 1 on the upper surface thereof is displayed on the display unit 12, as shown in FIG. 18 (Step S12). Then, the person under test mounts the living body measurement apparatus 1 with a tiptoe and a heel of the right foot contact to the current supplying electrode 2A and the voltage measurement electrode 3A, respectively, and with a tiptoe and a heel of the left foot contact to the current supplying electrode 2B and the voltage measurement electrode 3B, respectively.

Figure 19:
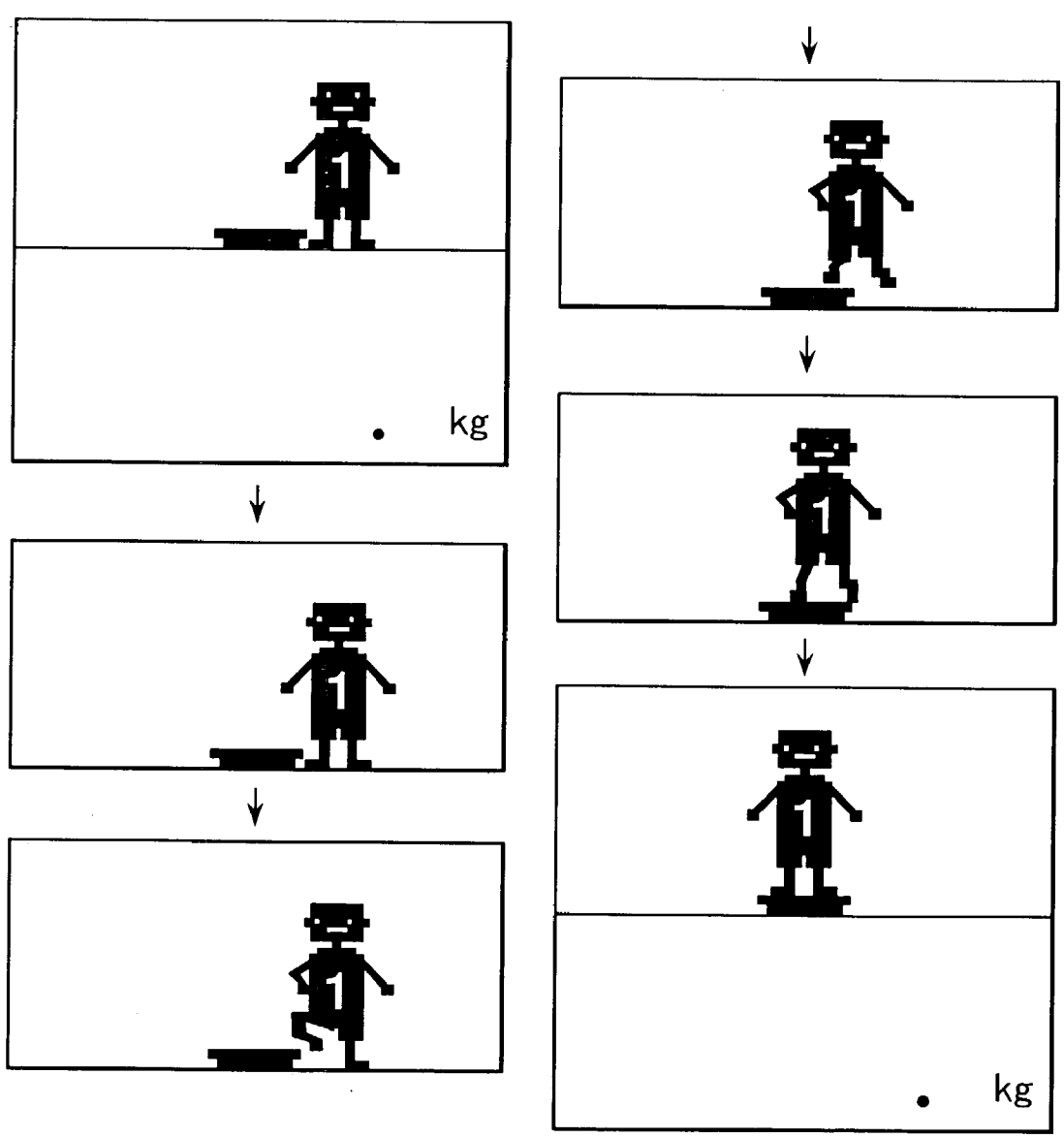
FIG. 19 is a display screen on which a character moves to show that the person under test mounts the living body measurement apparatus.

When the weight measurement circuit 6 detects a load the arithmetic and control circuit 10 determines that the person under test has mounted the living body measurement apparatus 1 and operates to display a sequence of animations on the display unit 12 for indicating such fact, as shown in FIG. 19.

Figure 20:
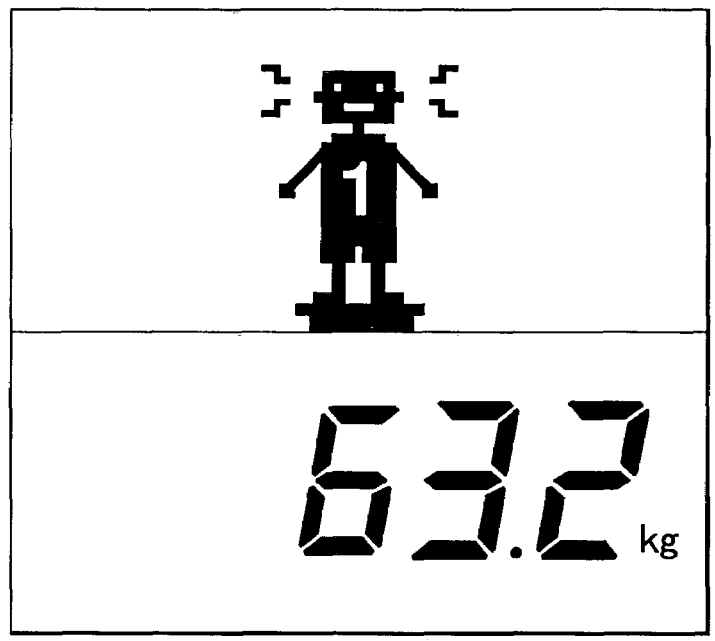
FIG. 20 is a display screen after the body weight of the person has been measured.
Figure 21:
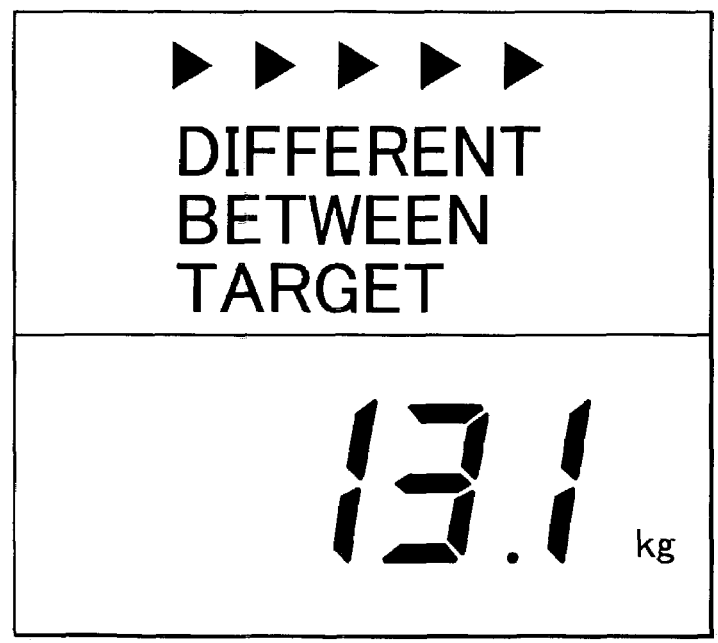
FIG. 21 is a display screen on which the difference between the measured body weight and the target body weight of the person is displayed.
Figure 22:
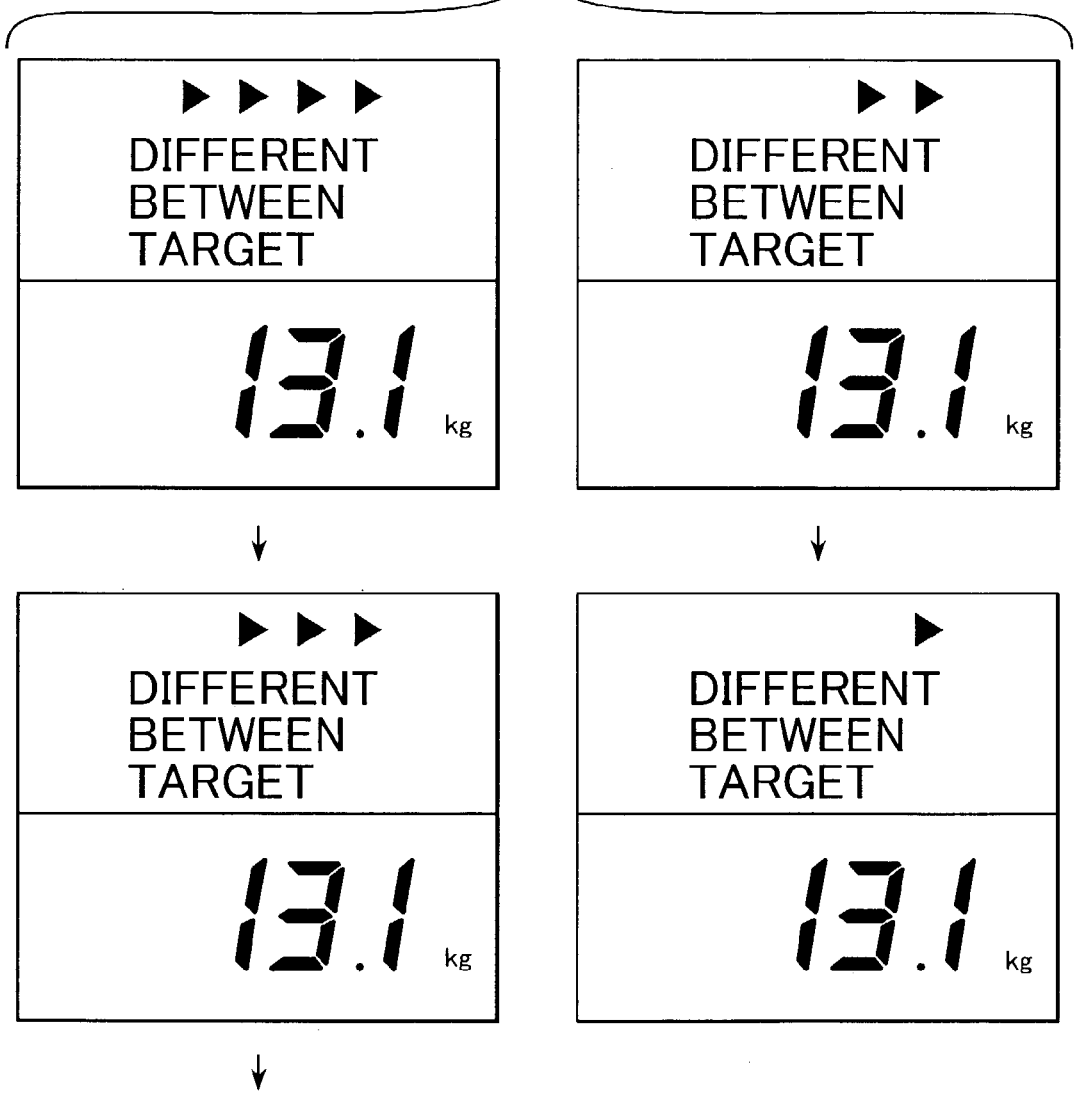
FIG. 22 is a display screen during the time interval that bioelectrical impedance is measured.

Then, the weight measurement circuit 6 measures the body weight of the person under test (Step S13). When the body weight is determined some display is presented on the display unit 12 for indicating the completion of measurement of the body weight, as shown in FIG. 20. In this example, the body weight of 63.2 kg is measured (Step S14). Then, the difference between the measured body weight and the target body weight is displayed in the lower section or the segmented display section of the display unit 12, as shown in FIG. 21. At the same time, a plurality of arrows is displayed in the upper section, together with the letters "DIFFERENCE BETWEEN TARGET". Then, the measurement of bioelectrical impedance is performed. An AC current from the RF constant current circuit 5 is supplied to the body of the person under test via the current supplying electrodes 2A and 2B, and the voltage across the voltage measurement electrodes 3A and 3B is measured with the voltage measurement circuit 5. Then, the arithmetic and control circuit 10 calculates the bioelectrical impedance for the person under test based on the measurement data (Step S15). In the meanwhile, in order to show that the living body measurement apparatus 1 is in the course of impedance measurement, the number of arrows on the display unit 12 is gradually reduced, as shown in FIG. 22.

Then, calculation of body fat rate for the person under test is performed based on the body weight and the bioelectrical impedance thus measured as well as the height data already entered. It is noted, here, that the computing equation used for calculation of the body fat rate is varied depending upon the sex and the age entered, and therefore, the arithmetic and control circuit 10 is necessary to select the most suitable computing equation for calculation. For detailed description for measurement and calculation of the body fat rate, refer to Japanese Patent Publication No. 5-49050 which is incorporated herein by a reference.

Figure 23:
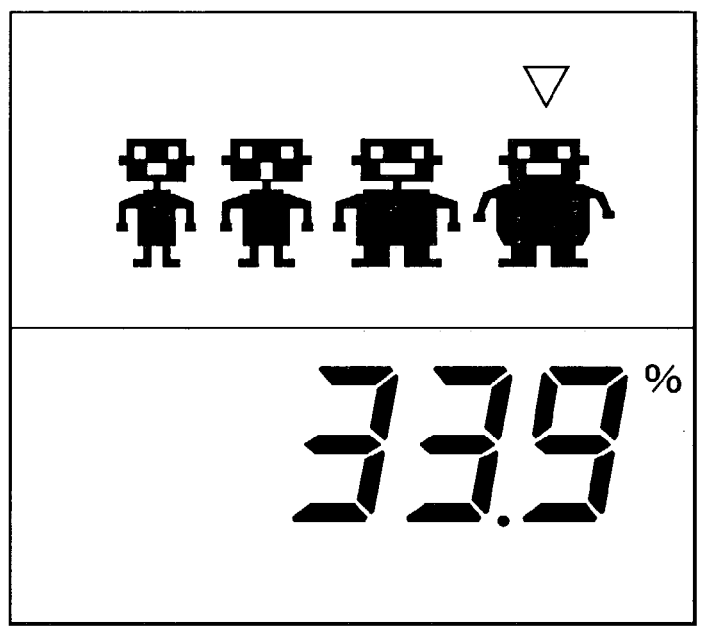
FIG. 23 is a display screen on which the body fat rate is displayed.

The calculated body fat rate is displayed in the lower section of the display unit 12 (Step S16). At the same time, a plurality of characters each having different lateral width is displayed in the dot-matrix display section of the display unit, as shown in FIG. 23. In this example, four kinds of characters are displayed in such order that the lateral width thereof gradually increased from left-most one to right-most one.

The characters are classified into four groups depending on the level of the calculated body fat rate. The four groups are: "slightly slender"; "standard"; "fattish"; and "adiposity". One of the characters is selected depending on which of the groups the calculated body fat rate belongs to. In this example, the right-most character is selected.

Figure 24:
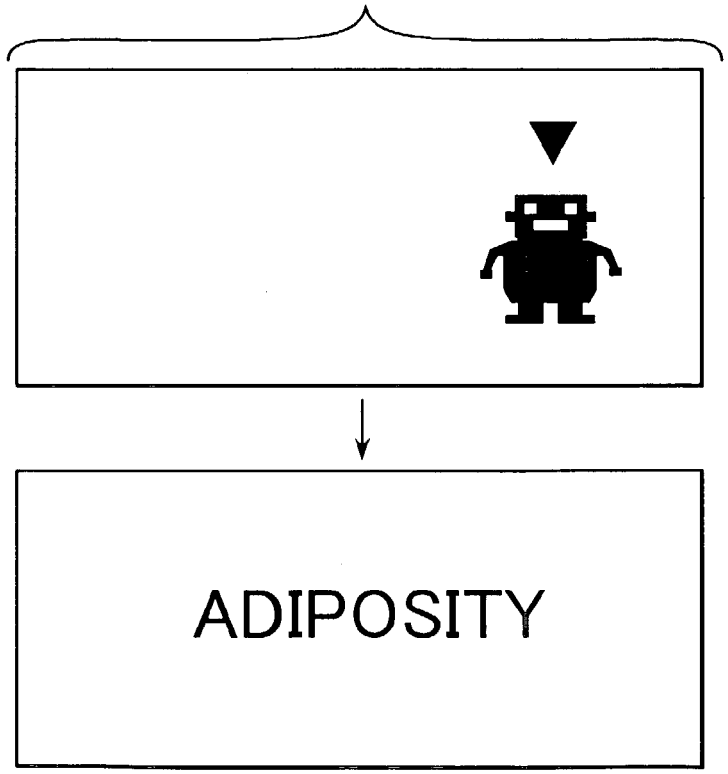
FIG. 24 is a display screen on which the result of evaluation for body fat rate is displayed.

Referring to FIG. 24, all the characters other than that selected are erased. In this example, only the character having largest lateral width is displayed, and therefore, it is obvious that the person under test is in non-desirable condition. However, in order to recognize the meaning of the character, the result of evaluation for the measurement data is additionally displayed by using the word or letters. In this example, the word "ADIPOSITY" is displayed to inform the result of evaluation.

While the character is displayed on the display unit 12 at Step S16 the arithmetic and control unit 10 performs the calculation of other body compositions (Step S17).

The arithmetic and control unit 10 calculates the visceral fat area or "VFA" for the person under test.

The visceral fat area "VFA" is calculated based on the height "Ht" (cm), the body weight "Wt" (kg) and the age "Age" by the computing equation:

$$VFA = A_1 \times Ht/Wt + B_1 \times FM + C_1 \times Age D_1$$

where $A_1$, $B_1$, $C_1$, and $D_1$ are constants.

"FM" in the above computing equation means fat mass that may be derived when the body fat rate is calculated in Step S16.

In this way, the visceral fat area "VFA" is derived and the level of visceral fat area is determined. In this example, the level 1 is defined as having VFA<20 cm$^2$; the level 2 is defined as having VFA of 10 cm$^2$ greater than the level 1; and so on.

Next, the visceral fat for the person under test is evaluated by determining whether it belongs to "standard"; "slightly excessive"; or "excessive" depending on the level of VFA. It is assumed, here, that the level 1 to 9 is defined as "standard" range; the level 10 to 14 is defined as "slightly excessive" range; and the level 15 or more is defined as "excessive" range.

Next, the arithmetic and control unit 10 calculates the basal metabolism for the person under test.

For detailed description of calculation of basal metabolism, refer to Japanese Patent Laid-Open No. 2002-112982. The basal metabolism "BMR" is calculated by the computing equation:

$$BMR = A_2 \times FFM^2 + B_2 \times FFM + C_2 \times (1/age) + D_2 \times body\ weight + E_2$$

where "BMR" is basal metabolism (Kcal/day), "FFM" is fat free mass (kg), and $A_2$, $B_2$, $C_2$, $D_2$, $E_2$ are constants.

The level of basal metabolism for the person under test is determined depending on the calculated BMR. In this example, the basal metabolism is evaluated as to whether it is in higher range, or in standard range, or in lower range.

Next, the arithmetic and control unit 10 performs calculation about the muscle of the person under test.

The muscle index "MI" is calculated based on the measured bioelectrical impedance and the body information of the person under test retrieved from the storage unit 15.

In this example, the value of fat free mass/height$^2$ is used as the muscle index "MI". This value is equal to Lean Mass Index "LMI" (fat free mass/heights$^2$), and therefore, it is calculated by the computing equation:

$$MI = BMI - FMI$$

where "BMI" is Body Mass Index, and "FMI" is Fat Mass Index (fat mass/height$^2$).

In the meanwhile, the display unit 12 continues to display the character selected when the body fat rate is evaluated, but it displays now the result of calculation performed in Step S17.

Because the results are displayed each for fixed time period the clock unit 14 is used for measuring the time. Every time when the fixed time period has passed (Step S18) a display counter in the storage unit 15 is incremented by one (Step S19).

Figure 25:
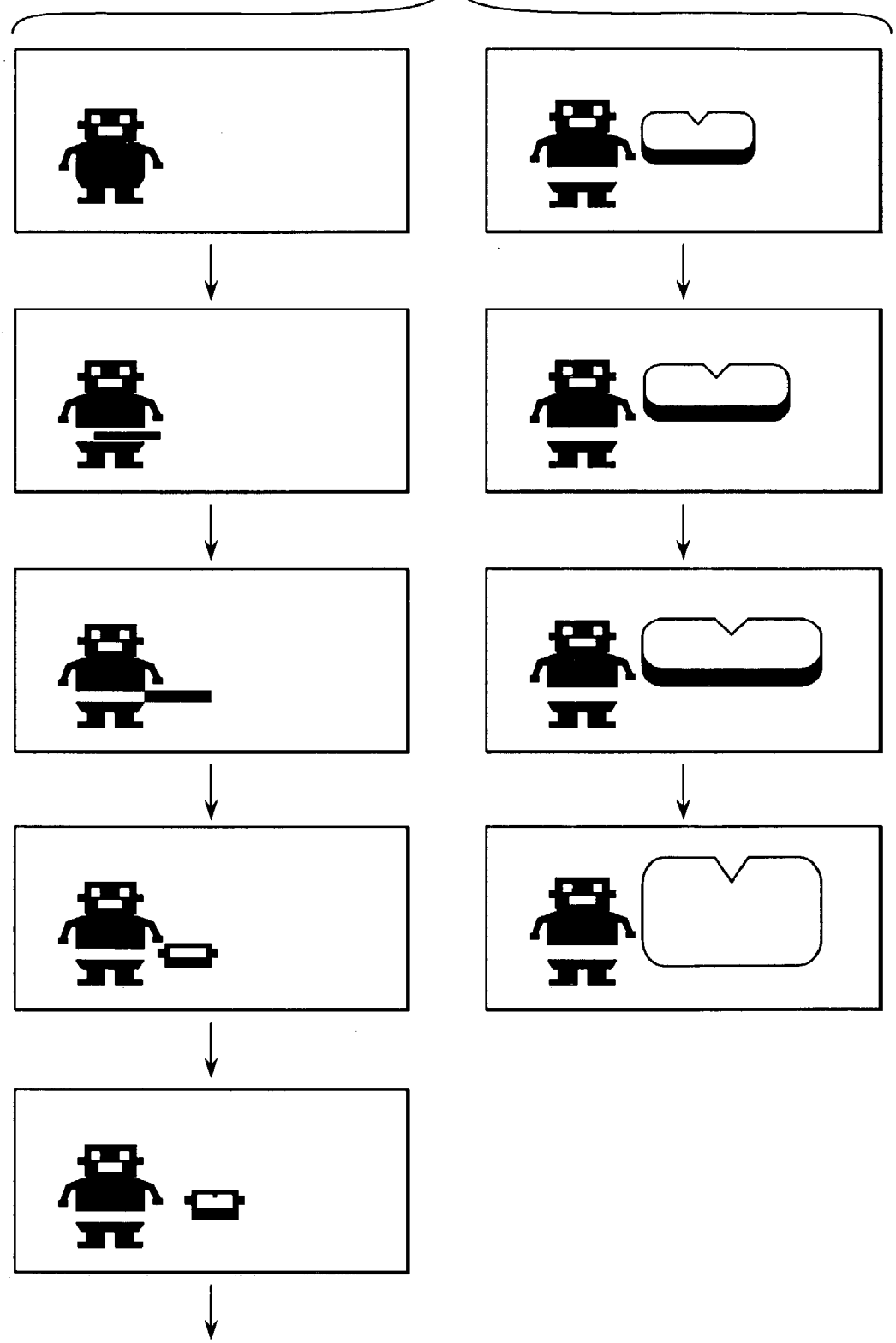
FIG. 25 is a display screen on which a transition to display of visceral fat for a person under test is gradually performed.
Figure 26:
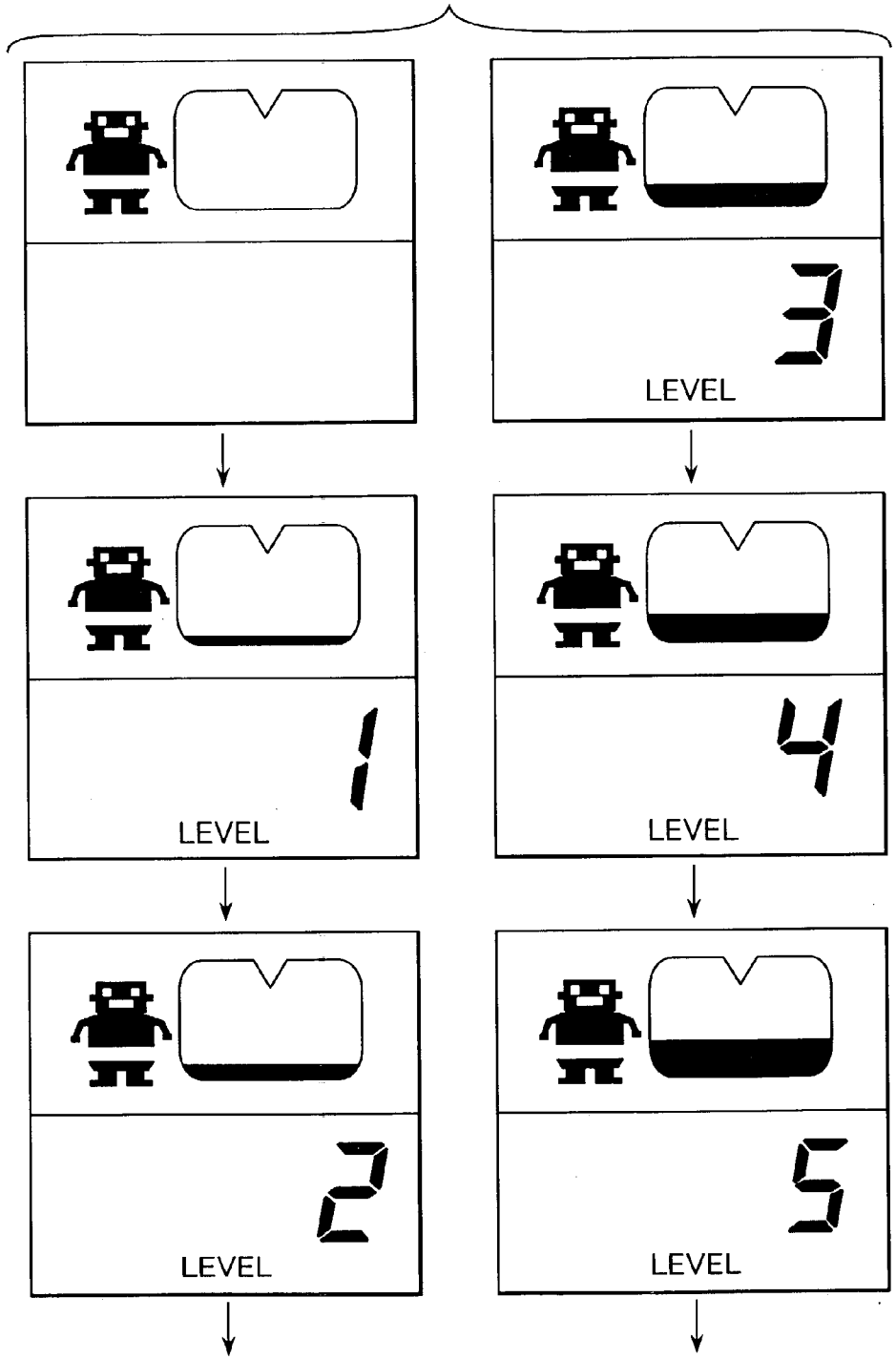
FIG. 26 is a display screen on which the visceral fat level displayed is successively increased.
Figure 27:
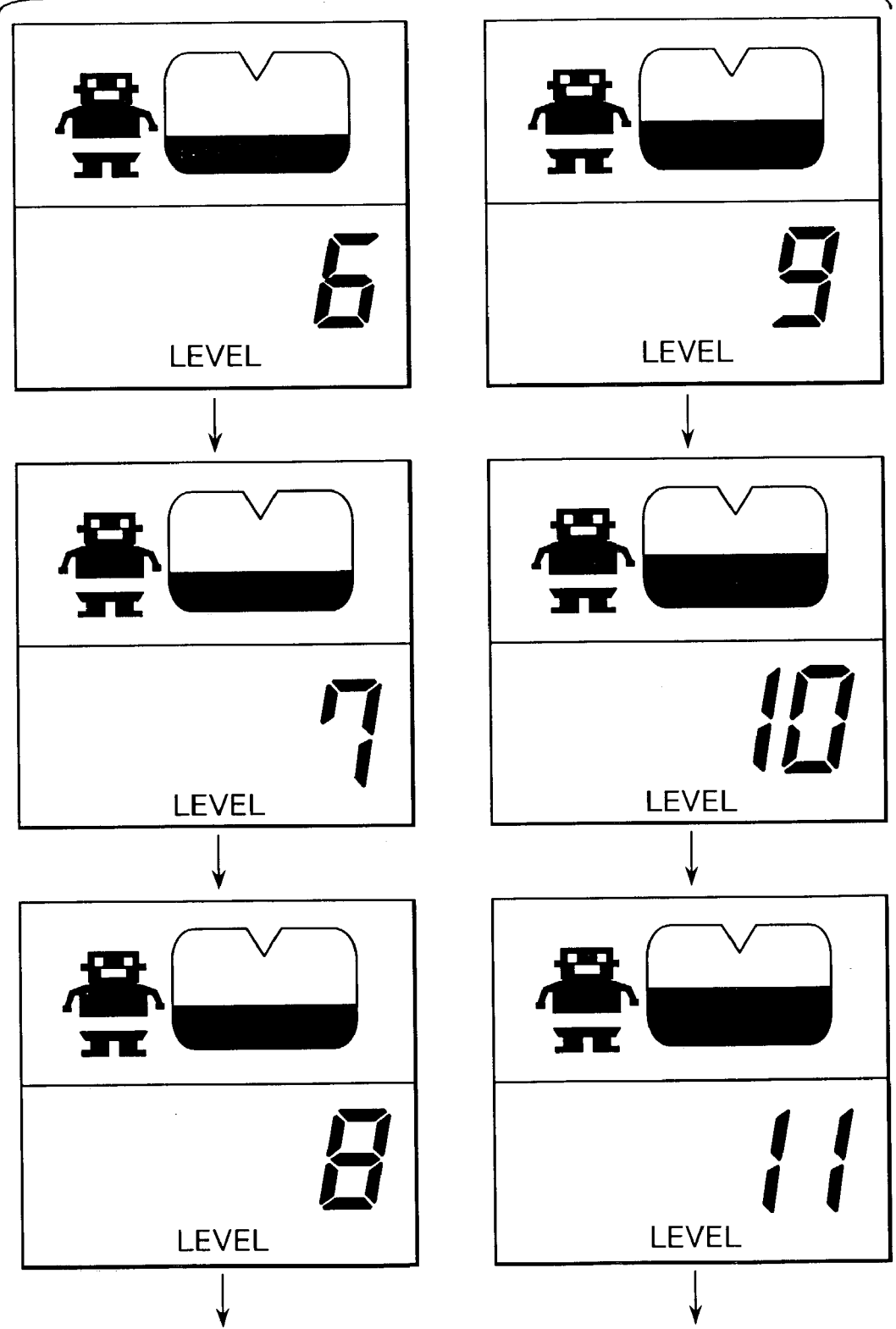
FIG. 27 is a display screen on which the visceral fat level displayed is successively increased.
Figure 28:
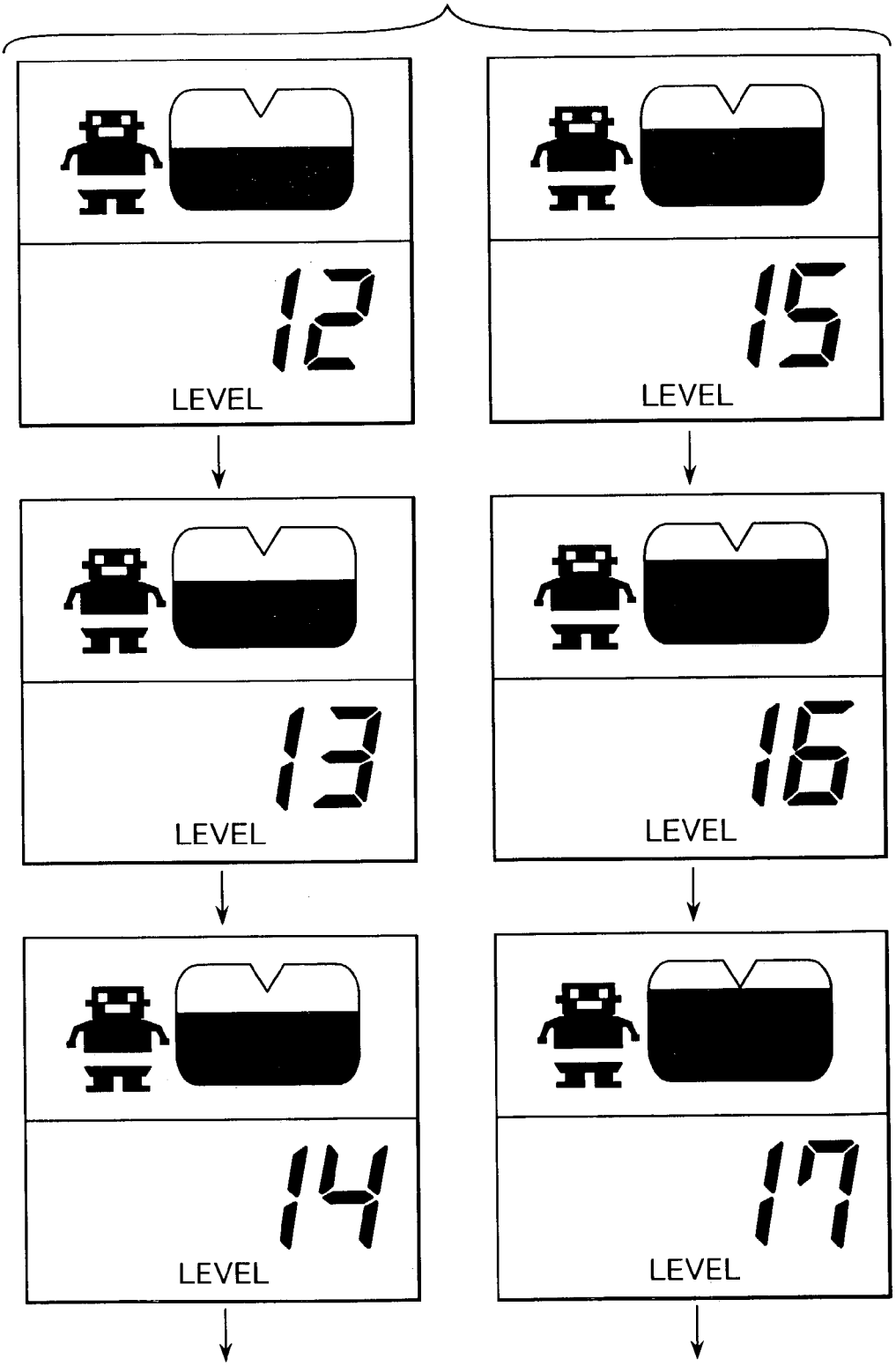
FIG. 28 is a display screen on which the visceral fat level displayed is successively increased.
Figure 29:
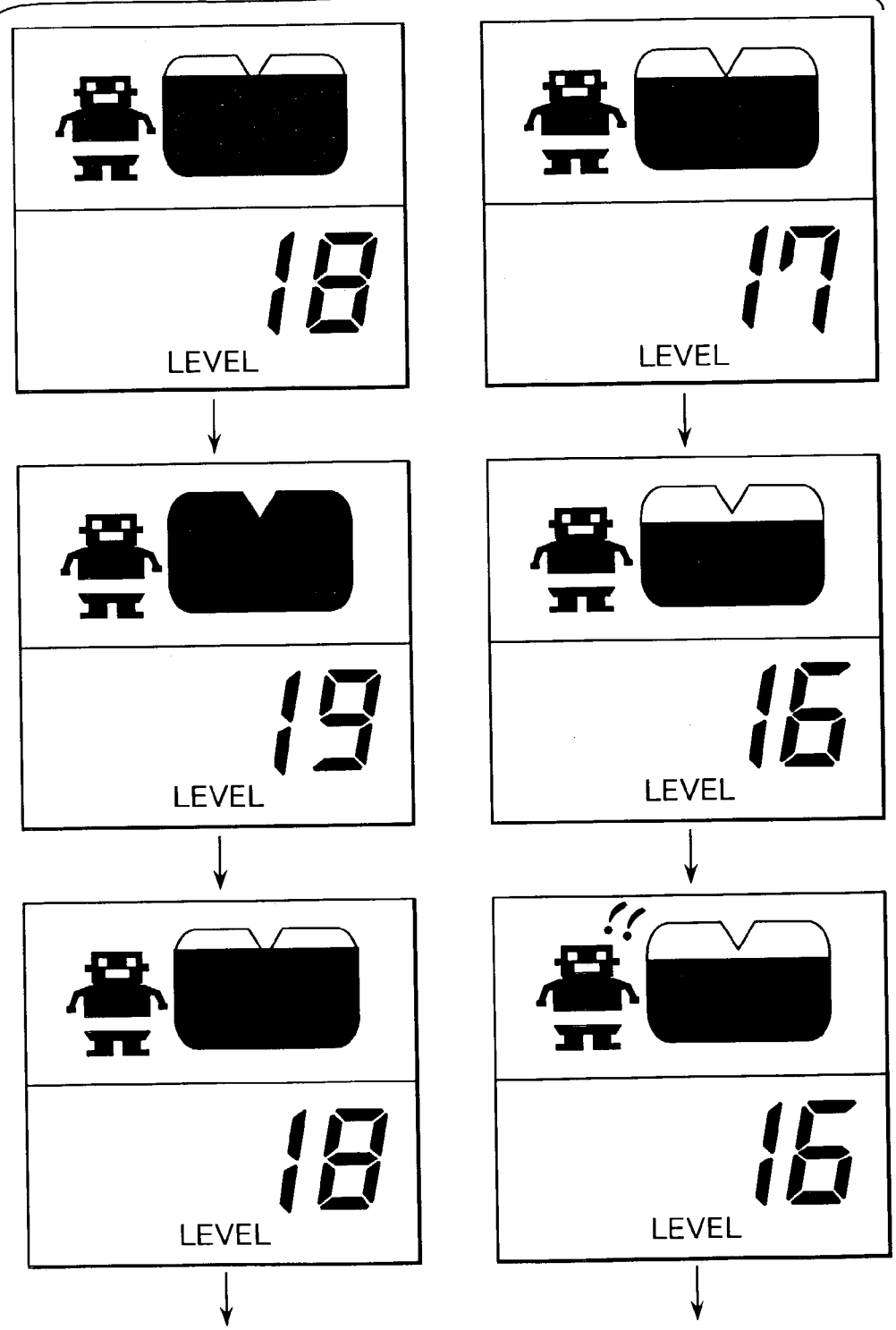
FIG. 29 is a display screen on which the visceral fat level displayed is successively increased.

Initially the display counter is at zero (Step S20) and the result for visceral fat is displayed. Referring to FIG. 25 the result of evaluation for visceral fat is displayed in such manner that only a slice of an abdomen of the character is taken. The dots displayed are gradually moved to produce an enlarged cross-section view of the abdomen of the character.

Figure 30:
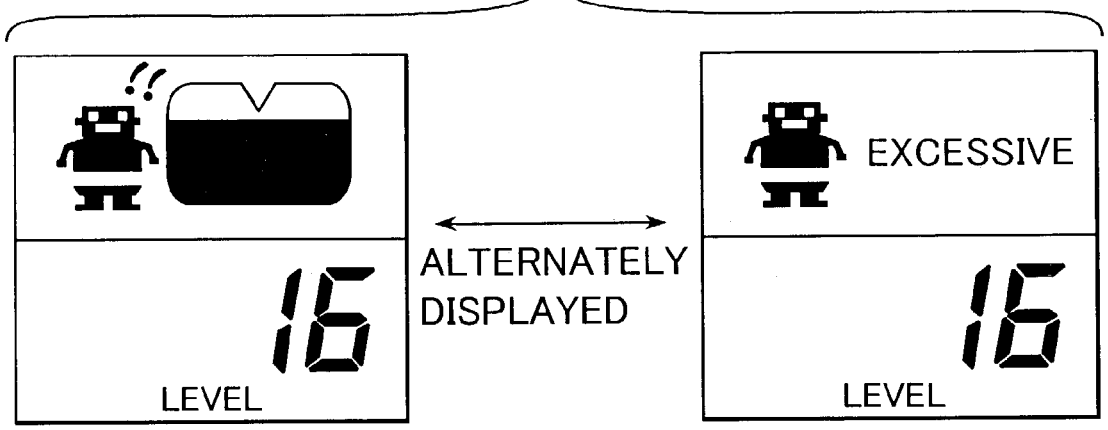
FIG. 30 is a display screen on which the result of visceral fat level is displayed.

Thereafter, the result of evaluation for visceral fat level is displayed, as shown in FIGS. 26 to 29. The number of dots that are turned ON to indicate an amount of visceral fat in the abdomen is increased with the increase in level number for the visceral fat. First of all, independently of the result of evaluation for visceral fat level, the display unit sequentially displays a set of animations each indicating the visceral fat level in the order starting from Level 1 at which all the dots showing the visceral fat are turned OFF toward Level 19 at which all the dots showing the visceral fat are turned ON. Assuming, here, that the result of evaluation for visceral fat is less than Level 19, the display unit is reversed to display the animations in the opposite order while turning OFF the dots and reducing the level number until the animation indicating the actual result of evaluation is displayed, upon which the display unit stops turning OFF of the dots and reduction in level number. In contrast thereto, assuming that the result of evaluation for visceral fat is greater than Level 19, the display unit keeps all the dots showing the visceral fat turned ON, but the level number displayed in the lower section of the display unit is increased accordingly (Step S21). FIGS. 26 to 29 shows the case where the result of evaluation for visceral fat is determined to be Level 16. In this connection, the animation indicating the result of evaluation for visceral fat may be displayed alternately with another animation indicating whether the evaluated visceral fat level number is "standard", "slightly excessive" or "excessive", as shown in FIG. 30.

After a fixed time interval the display counter is incremented to "1" and then the result for basal metabolism for a person under test is displayed (Step S22).

Figure 31A:
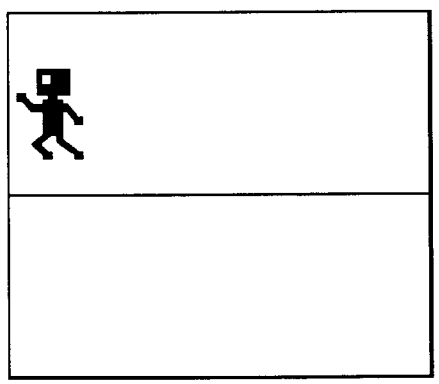
FIGS. 31A to 31D are a display screen on which basal metabolism for a person under test displayed is successively increased.
Figure 31B:
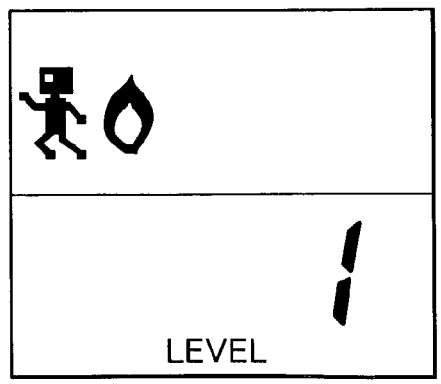
Figure 31C:
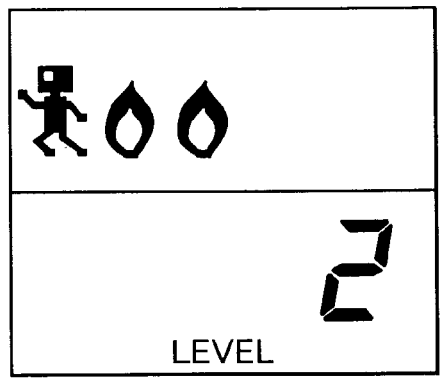
Figure 31D:
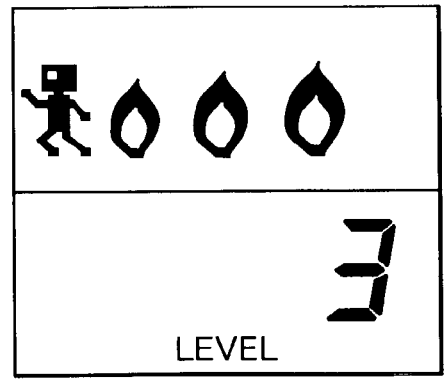

It is generally said that the physical constitution of a person having higher basal metabolism tends to burn further amount of body fat. Referring to FIGS. 31A to 31D, with the increase in number of flame marks displayed with a character, it can be imagined that further amount of body fat is burned. In particular, FIG. 31B shows a person who has lower basal metabolism; FIG. 31C shows a person who has standard basal metabolism; and FIG. 31D shows a person who has higher basal metabolism.

The result for basal metabolism is displayed in the following manner: At first, the display unit sequentially displays a set of animations: a first animation only indicating a character, as shown in FIG. 31A; a second animation indicating one flame mark, in addition to a character, as shown in FIG. 31B; a third animation indicating two flame marks, as shown in FIG. 31C; and a fourth animation indicating three flame marks, as shown in FIG. 31D. Thereafter, any one of the animations, as shown in FIGS. 31B to 31D is selected and displayed according to the determined basal metabolism (Step S23).

After a fixed time interval the display counter is incremented to "2" and then the result for muscle for a person under test is displayed (Step S24).

Figure 32A:
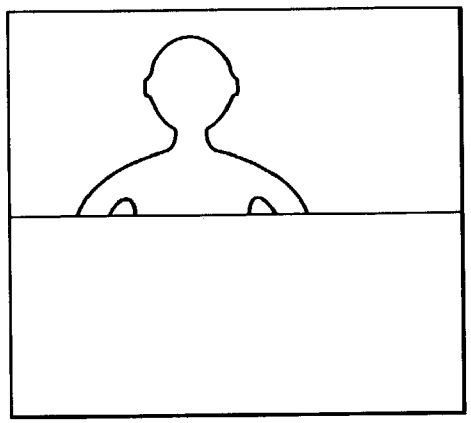
FIGS. 32A to 32D are a display screen on which muscle volume for a person under test displayed is successively increased.
Figure 32B:
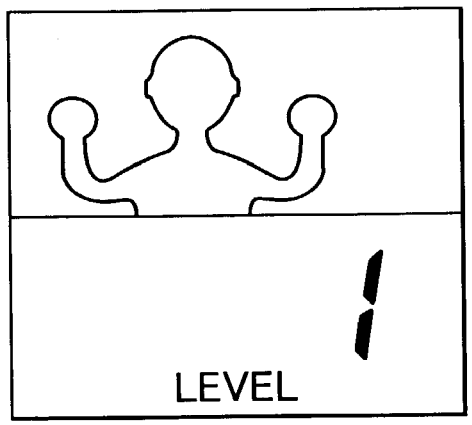
Figure 32C:
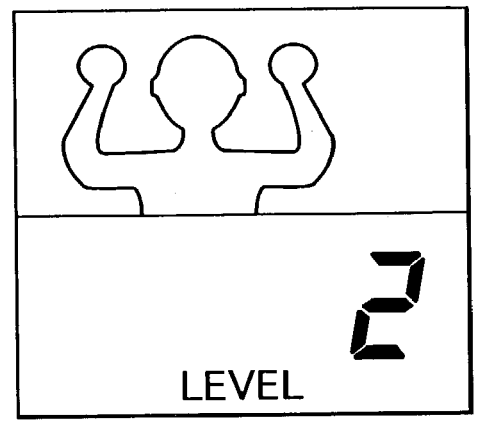
Figure 32D:
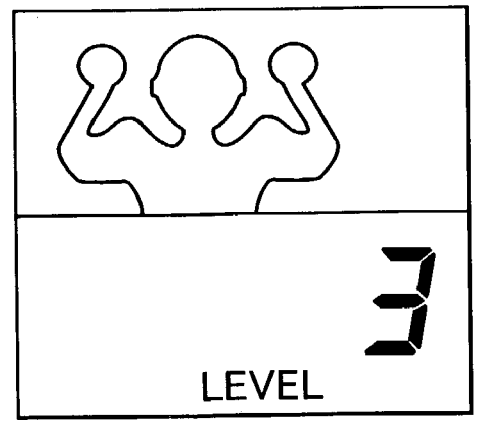

The result for muscle is displayed in three steps according to the calculated "MI" value. FIGS. 32A to 32D shows the result for muscle in which a volume of muscle can be imagined by gradually increasing the thickness of upper arms of a character. FIG. 32B shows a person who has lower volume of muscle; FIG. 32C shows a person who has standard volume of muscle; and FIG. 32D shows a person who has larger volume of muscle.

The result for muscle is displayed in the following manner: At first, the display unit sequentially displays a set of animations: a first animation only indicating a character, as shown in FIG. 32A; a second animation indicating thin upper arms of the character, as shown in FIG. 32B; a third animation indicating standard upper arms of the character, as shown in FIG. 32C; and a fourth animation indicating thick upper arms of the character, as shown in FIG. 32D. Thereafter, any one of the animations, as shown in FIGS. 32B to 32D is selected and displayed according to the calculated "MI" (Step S25).

After a fixed time interval the display counter is incremented to "3". Accordingly, the decision steps S20, S22 and S24 produce "negation" response so that all the measurement and display operations are terminated and the power for the living body measurement apparatus 1 is turned OFF (Step S26).

Figure 33:
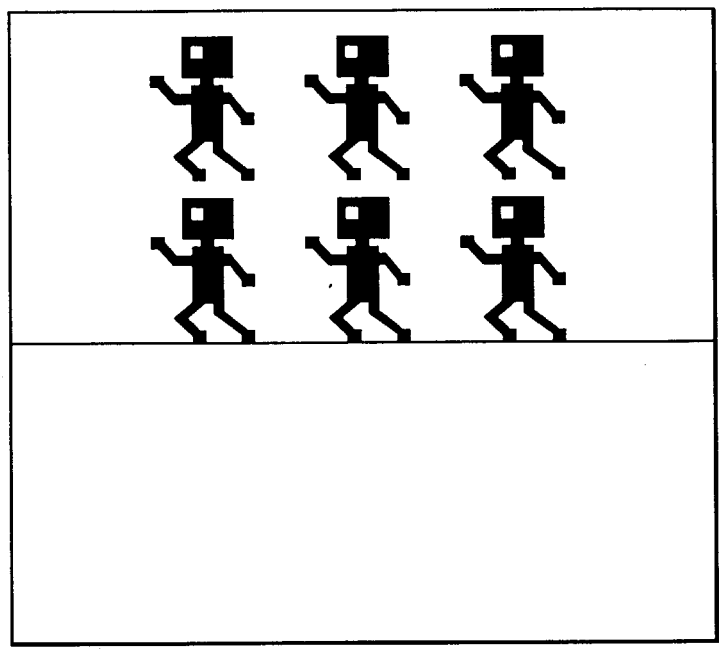
FIG. 33 is a display screen on which the basal metabolism for the person under test is displayed in alternative way.
Figure 34:
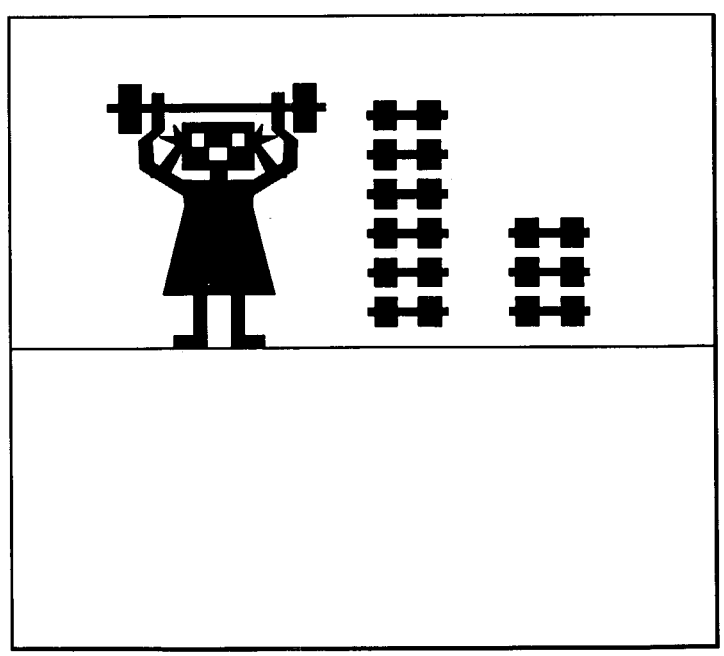
FIG. 34 is a display screen on which the muscle volume for the person under test is displayed in alternative way.

The present invention has been described above with reference to the preferred embodiments. However, the present invention is not limited to those described above, but it may be embodied in another form as long as it produces any readily understandable measurement result. For example, an animation indicating the basal metabolism for a person may be displayed in such manner that the number of runners is changed depending on the measurement result, as shown in FIG. 33. Furthermore, for a volume of muscle, an animation wherein the number of barbell is changed depending on the measurement result may be displayed, as shown in FIG. 34.

It is apparent from the foregoing that a living body measurement apparatus according to the present invention provides an animation or moving image making association with the actual condition of body composition for a person under test that has previously been displayed only in numerical value, whereby the measurement result can substantially be interpreted even by any child who can't read the letters and any foreigner who don't understand the language. Furthermore, because of the result of evaluation for body composition also displayed by using an animation, the person under test can conduct the measurement with great interest, which is useful in that the person is likely to continue the measurement for health care.

According to an embodiment, in addition to the animation, the numerical value may be given for displaying the measurement result. This is very useful because the person under test can understands the measurement result more concretely.

According to another embodiment, a plurality of characters each having different body build may be provided. Then, one most suitable character may be selected from among them based on the calculated body fat and displayed in the form of animation, which makes possible for a person under test to readily imagine how large the measurement result for body fat is, which is very useful for health care.

According to further embodiment, only a slice of an abdomen of the character may be taken based on the calculated visceral fat so that an enlarged cross-section view of the abdomen of the character is displayed in the form of animation using different color. Then, a person under test readily imagines what the evaluation result for visceral fat is, and therefore, such evaluation result is likely to remain in the person's memory, which is very useful for health care.

According to yet further embodiment, flame marks displayed in the form of animation may be changed in number depending on the calculated basal metabolism. Then, a person under test readily imagines what the evaluation result for basal metabolism is, and therefore, such evaluation result is likely to remain in the person's memory, which is very useful for health care.

According to yet further embodiment, upper arms of the character displayed in the form of animation may be changed in thickness depending on the calculated muscle volume. Then, a person under test readily imagines what the evaluation result for muscle volume is, and therefore, such evaluation result is likely to remain in the person's memory, which is very useful for health care.

What is claimed is:

1. A living body measurement apparatus, comprising:
an input unit;
a measurement unit;
an arithmetic unit; and
a display unit, wherein
said input unit enters body information for a person under test,
said measurement unit measures physical characteristic for the person under test,
said arithmetic unit calculates an index of body composition for the person under test based on the entered body information and the measured physical characteristic, and
said display unit includes a display section that displays the calculated index of body composition by using an animation in such manner that the animations is differently displayed according to the result of calculation by said arithmetic unit.

2. A living body measurement apparatus according to claim 1 wherein said display unit also displays some numerical value representing the calculated index of body composition.

3. A living body measurement apparatus according to claim 1 or 2 wherein said index of body composition is of body fat for the person under test and wherein said display unit simultaneously displays a plurality of characters each having different lateral width, the relevant one of which is selected according to the calculated body fat value to indicate the result of body fat for the person under test.

4. A living body measurement apparatus according to claim 1 or 2 wherein said index of body composition is of visceral fat for the person under test and wherein said display unit specifically displays an abdominal region of the character in enlarged view and identifies it by different color selected according to the calculated visceral fat value to indicate the result of visceral fat for the person under test.

5. A living body measurement apparatus according to claim 1 or 2 wherein said index of body composition is of basal metabolism for the person under test and wherein said display unit changes the number of flame marks according to the calculated basal metabolism value to indicate the result of basal metabolism for the person under test.

6. A living body measurement apparatus according to claim 1 or 2 wherein said index of body composition is of muscle for the person under test and wherein said display unit changes the thickness of an upper arm of the character according to the calculated muscle value to indicate the result of muscle for the person under test.

* * * * *